US00PP19401P2

(12) United States Plant Patent
Heins

(10) Patent No.: US PP19,401 P2
(45) Date of Patent: Nov. 4, 2008

(54) ***BEGONIA*PLANT NAMED 'BEGO 538'**

(50) Latin Name: *Begonia×tuberhybrida*
Varietal Denomination: BEGO 538

(75) Inventor: Christiane Heins, Münden (DE)

(73) Assignee: Benary Samenzucht GmbH of Hann., Münden (DE)

( * ) Notice: Subject to any disclaimer, the term of this patent is extended or adjusted under 35 U.S.C. 154(b) by 0 days.

(21) Appl. No.: 11/881,797

(22) Filed: Jul. 27, 2007

(51) Int. Cl.
*A01H 5/00* (2006.01)

(52) U.S. Cl. ..... Plt./347
(58) Field of Classification Search ..... Plt./347
See application file for complete search history.

(56) References Cited

PUBLICATIONS

UPOV–ROM GTITM, Plant Variety Database Jun. 2007, GTI Jouve Retrieval Software, Citation for Begonia 'Bego 538', one page.*

* cited by examiner

*Primary Examiner*—Kent L. Bell
*Assistant Examiner*—June Hwu
(74) *Attorney, Agent, or Firm*—C. A. Whealy

(57) ABSTRACT

A new and distinct cultivar of *Begonia* plant named 'BEGO 538', characterized by its compact and mounded plant habit; freely basal branching habit; relatively small leaves; and numerous flowers that are bright orange red in color.

1 Drawing Sheet

Botanical designation: *Begonia×tuberhybrida.*
Cultivar denomination: 'BEGO 538'.

BACKGROUND OF THE INVENTION

The present invention relates to a new and distinct cultivar of *Begonia* plant, botanically known as *Begonia× tuberhybrida,* commercially known as hybrid tuberose *Begonia,* and hereinafter referred to by the name 'BEGO 538'.

The new *Begonia* is a product of a planned breeding program conducted by the Inventor in Hann. Münden, Germany. The objective of the breeding program was to develop new freely branching hybrid tuberose *Begonia* cultivars with small leaves and numerous flowers.

The new *Begonia* originated from a cross-pollination made by the Inventor in June, 2001 of a proprietary selection of *Begonia×tuberhybrida* identified as code number Fu 41/5, not patented, as the female, or seed, parent with an unidentified selection of *Begonia sutherlandii,* not patented, as the male, or pollen, parent. The new *Begonia* was discovered and selected by the Inventor from within the progeny of the stated cross-pollination in a controlled environment in Hann. Münden, Germany during the summer of 2002.

Asexual reproduction of the new *Begonia* by cuttings in a controlled environment in Hann. Münden, Germany since the fall of 2002, has shown that the unique features of this new *Begonia* are stable and reproduced true to type in successive generations.

SUMMARY OF THE INVENTION

The cultivar BEGO 538 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'BEGO 538'. These characteristics in combination distinguish 'BEGO 538' as a new and distinct cultivar of *Begonia:*

1. Compact and mounded plant habit.
2. Freely basal branching habit.
3. Relatively small leaves.
4. Numerous flowers that are bright orange red in color.

Plants of the new *Begonia* differ from plants of the female parent selection in the following characteristics:

1. Plants of the new *Begonia* are more freely branching and have thinner stems than plants of the female parent selection.
2. Plants of the new *Begonia* have smaller leaves than plants of the female parent selection.
3. Plants of the new *Begonia* have lighter-colored flowers than plants of the female parent selection.

Plants of the new *Begonia* differ from plants of the male parent selection in the following characteristics:

1. Plants of the new *Begonia* are larger and have thicker stems than plants of the male parent selection.
2. Plants of the new *Begonia* have larger leaves than plants of the male parent selection.
3. Plants of the new *Begonia* have larger and fuller flowers than plants of the male parent selection.

Plants of the new *Begonia* can also be compared to plants of the cultivar Helene Harms, not patented. In side-by-side comparisons conducted in Hann. Münden, Germany, plants of the new *Begonia* differed from plants of the cultivar Helene Harms in the following characteristics:

1. Plants of the new *Begonia* were larger than plants of the cultivar Helene Harms.
2. Leaves of plants of the new *Begonia* were larger than Leaves of plants of the cultivar Helene Harms.

3. Plants of the new *Begonia* and the cultivar Helene Harms differed in flower color as plants of the cultivar Helene Harms had yellow-colored flowers.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the bottom of the sheet comprises a side perspective view of a typical flowering plant of 'BEGO 538' grown in a container.

The photograph at the top of the sheet is a close-up view of typical flowers of 'BEGO 538'.

DETAILED BOTANICAL DESCRIPTIONS

In the following description, color references are made to The Royal Horticultural Society Colour Chart, 1995 Edition, except where general terms of ordinary dictionary significance are used. Plants used for the aforementioned photograph and following observations and measurements were grown in Ogden, Utah in 15.25-cm containers and under commercial practice in a polycarbonate-covered greenhouse during the spring and summer. During the production of the plants, day temperatures averaged 24° C. night temperatures averaged 21° C. and light levels were about 4,000 foot-candles. Plants used for the photograph and the description were about two months from planting.

Botanical classification: *Begonia×tuberhybrida* cultivar BEGO 538.

Parentage:

*Female, or seed, parent.*—Proprietary selection of *Begonia×tuberhybrida* identified as code number Fu 41/5, not patented.

*Male, or pollen, parent.*—Unidentified selection of *Begonia sutherlandii,* not patented.

Propagation:

*Type.*—By terminal vegetative cuttings.

*Time to initiate roots, summer.*—About 10 to 14 days at temperatures of about 20° C. to 22° C.

*Time to initiate roots, winter.*—About 14 to 16 days at temperatures of about 18° C. to 20° C.

*Time to produce a rooted young plant, summer.*—About four weeks at temperatures of about 20° C.

*Time to produce a rooted young plant, winter.*—About five weeks at temperatures of about 20° C.

*Root description.*—Fine, fibrous; 164C in color. Plants of the new *Begonia* have not been observed to form tubers.

*Rooting habit.*—Freely branching; moderately dense.

Plant description:

*Plant form.*—Compact and mounded plant habit; freely basal branching with about eight to nine primary branches per plant; primary branches with secondary branches at potentially every node. Vigorous and moderate growth rate.

*Plant height.*—About 15 cm.

*Plant width.*—About 30 cm.

*Branch description.*—Length: About 11.5 cm. Diameter: About 6 mm. Internode length: About 1.5 cm. Texture: Smooth, glabrous. Color: 182B.

*Leaf description.*—Arrangement: Simple, alternate. Length: About 7 cm. Width: About 4.2 cm. Shape: Roughly ovate. Apex: Acute. Base: Obliquely cordate. Margin: Erose. Texture, upper and lower surfaces: Smooth, glabrous. Venation pattern: Palmate; reticulate. Color: Developing leaves, upper surface: 146A with intervenal areas of 178B. Developing leaves, lower surface: 178A. Fully expanded leaves, upper surface: 147A with intervenal areas of 176A; venation, 146A. Fully expanded leaves, lower surface: 178A; venation, 148A. Petiole length: About 3.4 cm. Petiole diameter: About 3 mm. Petiole texture, upper and lower surfaces: Smooth, glabrous. Petiole color, upper and lower surfaces: 166D. Petiole color, lower surface: 183D.

Flower description:

*Flowering habit.*—Rounded axially flowers with numerous tepals. Freely flowering habit with about 17 to 20 flowers and flower buds per branch. Flowers positioned mostly outwardly arising from below the foliage. Flowers not fragrant.

*Natural flowering season.*—Plants flower continuously during the spring in Germany. Flowers last about five days on the plant. Flowers persistent.

*Flowers.*—Shape: Rounded to oval; rose-like. Diameter: About 3 cm. Depth (height): About 1.4 cm.

*Flower buds.*—Shape: Ovoid. Length: About 1.3 cm. Diameter: About 2 cm. Color: Close to 39A.

*Tepals.*—Arrangement: Rosette. Quantity per flower: Usually about 15 per flower arranged in about five or six whorls. Length: About 1.5 cm. Width: About 1.5 cm. Shape: Obovate. Apex: Rounded, obtuse. Base: Acute. Margin: Entire. Texture, upper and lower surfaces: Smooth, glabrous; velvety. Color: When opening, upper surface: 33A. When opening, lower surface: 33B. Fully opened, upper surface: 33B; towards the base, 19B. Color becoming closer to 30B with development. Fully opened, lower surface: 33C. Color becoming closer to 30C with development.

*Flower bracts.*—Quantity/arrangement. Two, opposite. Length: About 1.4 cm. Diameter: About 1.7 cm. Shape: Oval. Apex: Obtuse. Base: Obtuse. Margin: Entire. Texture, upper and lower surfaces: Glabrous, smooth; velvety. Color, upper surface: 31B. Color, lower surface: 35B.

*Peduncles.*—Angle: About 45° from vertical. Length: About 4 cm. Diameter: About 2 mm. Texture: Smooth, glabrous. Color: 182C.

*Reproductive organs.*—Stamens: None observed. Pistils: None observed.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 5° C. to about 40° C.

It is claimed:

1. A new and distinct *Begonia* plant named 'BEGO 538' as illustrated and described.

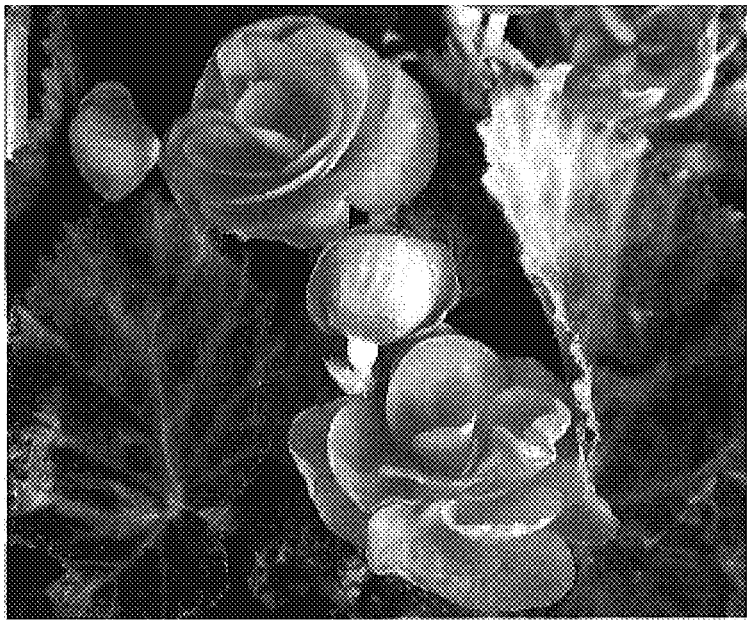
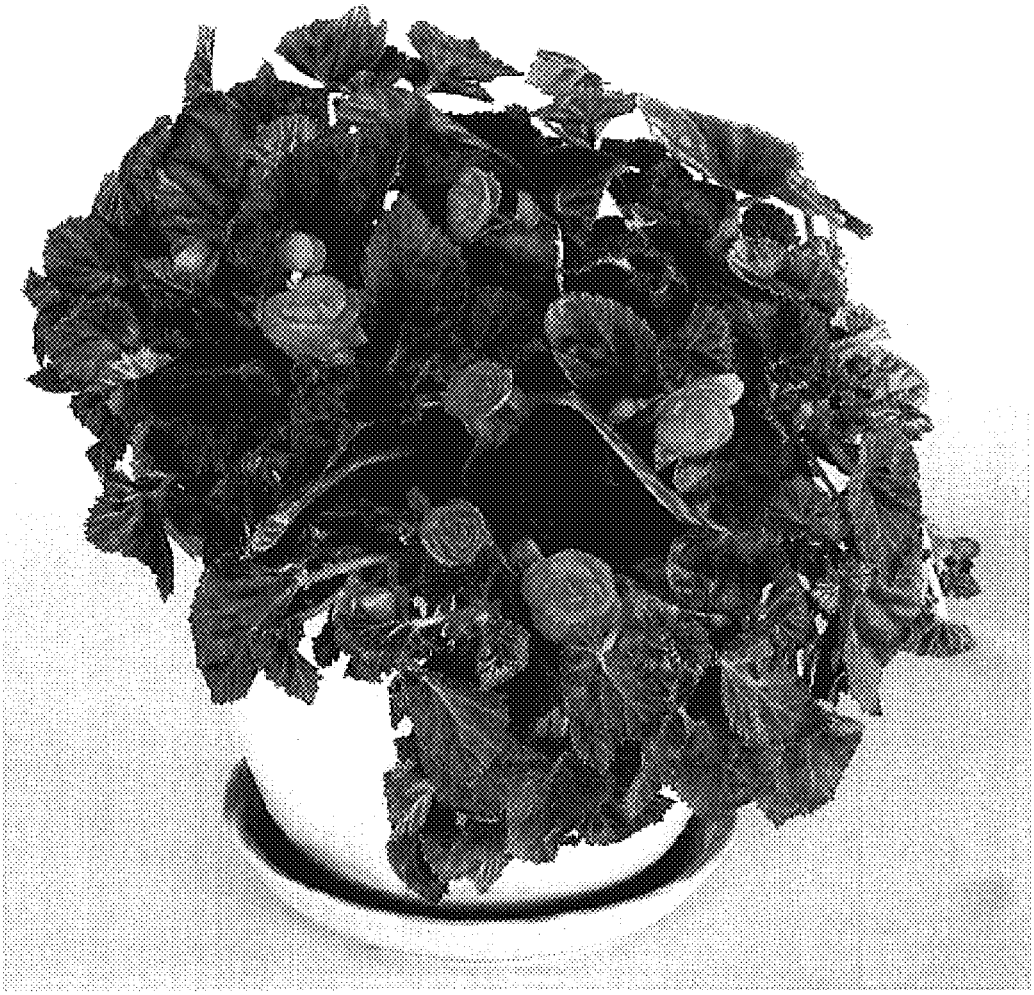

* * * * *